United States Patent [19]

Mizukami et al.

[11] Patent Number: 5,380,907
[45] Date of Patent: Jan. 10, 1995

[54] METHOD FOR PREPARING AROMATIC CARBONATE

[75] Inventors: Masamichi Mizukami; Katsushige Hayashi; Katsuhiro Iura; Takao Kawaki, all of Tsukuba, Japan

[73] Assignee: Mitsubishi Gas Chemical Company, Inc., Tokyo, Japan

[21] Appl. No.: 69,604

[22] Filed: Jun. 1, 1993

[30] Foreign Application Priority Data

Jun. 1, 1992 [JP] Japan .................... 4-140598

[51] Int. Cl.$^6$ .............................. C07C 69/96
[52] U.S. Cl. ..................... 558/270; 558/274
[58] Field of Search ................ 558/260, 270, 274

[56] References Cited

U.S. PATENT DOCUMENTS 4,187,242  2/1980  Chalk .................... 558/260

Primary Examiner—José G. Dees
Assistant Examiner—Joseph M. Conrad, III
Attorney, Agent, or Firm—Sughrue, Mion, Zinn, Macpeak & Seas

[57] ABSTRACT

A process for producing an aromatic carbonate which comprises:

reacting
(a) an aromatic hydroxy compound with
(b) carbon monoxide in the presence of
(c) an oxidation agent,
(d) a catalyst comprising a palladium compound or impregnated palladium catalyst,
(e) a co-catalyst comprising a manganese compound, a cobalt compound or a copper compound, and
(f) at least one nitrile compound at a temperature of 20° to 300° C.

12 Claims, No Drawings

METHOD FOR PREPARING AROMATIC CARBONATE

FIELD OF THE INVENTION

The present invention relates to a method for preparing aromatic carbonates, which are useful as raw materials for aromatic polycarbonates using a molten ester exchange method, i.e., a non-phosgene method. In more detail, the present invention relates to a method for preparing aromatic carbonates by reacting aromatic hydroxy compounds with carbon monoxide, in the presence of a palladium catalyst, a co-catalyst, an oxidizing agent and a nitrile compound.

BACKGROUND OF THE INVENTION

Conventionally, aromatic carbonates have been prepared by a reaction of aromatic hydroxy compounds with phosgene. However, phosgene is extremely toxic and highly corrosive. In addition, a large amount of alkali is necessary for neutralization of the hydrogen chloride produced as a by-product. Thus, development of a method in which phosgene is not used has been desired, and several attempts have been made. (Japanese Patent Application (OPI) Nos. Sho 60-169445 (U.S. Pat. No. 4,552,704), Hei 1-93560 (U.S. Pat. No. 5,166,393), and Japanese Patent Publication No. Sho 56-42577).

However, sufficient yield and production rate have not been obtained, since the equilibrium is extremely offset to the raw material side in this equilibrium reaction. Further, the step is complex since the step involves a two-stage reaction which is achieved by way of aliphatic and aromatic carbonates.

So, methods for preparing an aromatic carbonate in a single-stage, in which an aromatic hydroxy compound is oxidatively carboxylated in the presence of carbon monoxide and an oxidizing agent, have been proposed. For example, Japanese Patent Publication Nos. Sho 53-68747 (U.S. Pat. No. 4,096,168), Sho 54-135743, Sho 54-135744, Sho 55-102539, Hei 2-104564, Hei 2-142754, Hei 1-165551, are known.

Japanese Patent Publication No. Sho 56-38143 discloses the reaction of phenol with palladium in the presence of a base. However, this method is not a catalytic reaction and a stoichiometric amount of palladium is required. Thus, this method is not industrially advantageous.

Next, Japanese Patent Publication Nos. Sho 56-38144 and Sho 56-38145 disclose a method in which less than the stoichiometric amount of palladium is used. This method comprises preparing aromatic carbonates by reacting phenols with carbon monoxide and oxygen in the presence of a palladium catalyst, and a redox agent for conversion of reduced O-valent palladium into divalent palladium is co-present in order for the palladium to act in the nature of a catalyst.

However, addition of a base is essential in the above-mentioned method. Further, Japanese Patent Publication No. Sho 56-38145 discloses an improvement in this method in which a drying agent is added. However, the reaction system is complex.

Further, the reaction system is more complex in Japanese Patent Application Nos. Sho 54-135743, Sho 54-135744, etc., i.e., a phase transfer catalyst is added, etc.

In addition, Japanese Patent Application Nos. Hei 2-104564 and Hei 2-142754 are examples in which no base is added, however, tetraalkylammonium halide and quinone other than a catalyst and co-catalyst (redox agent) are essential. Thus, the system is not only complex, but also a problem in industrial applicability occurs.

EP 450 442 A1 discloses a method in which carbon dioxide is added as a drying agent, however, the system is complex, because a quaternary ammonium salt and quinone are used.

Japanese Patent Application No. Hei 1-165551 discloses a method for obtaining diphenyl carbonate in a system comprising palladium, iodide salts and zeolite. However, recovery of the objective material from the iodide product is difficult, and further, the reaction conditions require agitation in the presence of a large amount of zeolite.

SUMMARY OF THE INVENTION

As mentioned above, in all conventional catalyst systems, the yield of the desired product is low and the reaction rate is not sufficient. Additionally, the system is not satisfactory from an industrial view point, i.e., recovery of catalyst and separation of the desired product is difficult, etc.

In view of the problems of these conventional processes, the present invention offers a method capable of preparing aromatic carbonates without limitation in terms of the apparatus material, and with a high reaction rate and with high yield.

As a result of extensive research, it has now been found that aromatic carbonates can be obtained with good yield using an extremely simple method where unexpectedly a nitrile compound which is neutral and easy to handle is also present in the reaction system.

That is, the present invention provides a method for preparing an aromatic carbonate, which comprises reacting (a) an aromatic hydroxy compound with (b) carbon monoxide, in the presence of (c) a catalyst selected from the group consisting of palladium and palladium compound, (d) a co-catalyst selected from the group consisting of an Mn compound, Co compound and Cu compound, (e) oxidizing agent and (f) at least one nitrile compound.

A characteristic of the present invention lies in the ability to obtain an aromatic carbonate with good yield even though the system is extremely simple. That is, according to the present invention, an aromatic carbonate can be obtained with good yield, simply by adding a nitrile into a system comprising an aromatic hydroxy compound, a palladium or palladium compound, a co-catalyst and an oxidizing agent. This is particularly advantageous in handling, recovery and cost, in comparison with the use of amines, not to mention the use of quaternary salt and quinone.

DETAILED DESCRIPTION OF THE INVENTION

Suitable aromatic hydroxy compounds which can be used in the present invention are any compound in which a hydroxyl group is bonded directly to an aromatic ring. For example, alkyl phenols such as phenol, cresol, xylenol, dimethylphenol, trimethylphenol, tetramethylphenol, ethylphenol, propylphenol, benzylphenol, bisphenol A; halogenated phenols such as chlorophenol, bromophenol, dichlorophenol, dibromophenol; alkyl halogen substituted phenols such as methylchlorophenol, ethylchlorophenol, methylbromophenol, ethylbromophenol; phenols in which an alkyl or aryl group is bonded to the aromatic ring through a hetero atom, such as anisole, phenoxyphenol, phenylthiophenol, etc. (all isomer forms of the above-described compounds can be used).

Appropriate nitrile compounds which can be used in the present invention are compounds which contain a cyano group in the molecule. Typical examples include aliphatic nitriles such as acetonitrile, propionitrile, butyronitrile (isomers), pentenonitrile (isomers), hexenedinitrile (isomers), malononitrile, succinonitrile, adiponitrile, etc.; aromatic nitriles such as benzonitrile, phthalonitrile; etc.; and aromatic aliphatic nitriles such as phenylacetonitrile; and substituted compounds thereof. In the practice of the present invention, any nitrile may be used, however, acetonitrile, n-butyronitrile, and benzonitrile are preferred.

The amount of nitrile used generally is in the range from 0.0001 to 100 mole, preferably from 0.01 to 10 mole, more preferably from 0.1 to 10 mole, based on 1 mole of aromatic hydroxy compound.

Palladium or palladium compound is preferred as a catalyst in the present invention. Palladium or palladium compounds which can be used preferably in the present invention are elemental palladium and compounds which contain palladium as a component, and the oxidation state is not limited.

Examples of such catalysts are Pd black; supported palladium catalysts, such as $Pd/C$, $Pd/Al_2O_3$, $Pd/TiO_2$, $Pd/ZnO_2$, $Pd/BaSO_4$, $Pd/CaCl_3$, $Pd/asbestos$, $Pd/zeolite$, $Pd/molecular\ sieve$, etc.; alloy or inter-metal compounds, such as Pd-Pb, Pd-Se, Pd-Te, Pd-Hg, Pd-Tl, Pd-P, Pd-Cu, Pd-Ag, Pd-Fe, Pd-Co, Pd-Ni, Pd-Rh, etc.; these alloys or inter-metal compounds supported on supports, such as those mentioned above; inorganic salts, such as $PdCl_2$, $PdBr_2$, $PdI_2$, $PdSO_4$, $Pd(NO_3)$, etc.; organic acid salts, such as palladium acetate, palladium oxalate, etc.; $Pd(CN)_2$; PdO; PdS; palladium acid salts designated as $M_2[PdX_4]$, $M_2[PdX_6]$ (where M is an alkali metal such as Na, K, etc. or an ammonium ion, X is a nitro group, a cyano group or a halogen atom); amine complexes of palladium, such as $[Pd(NH_3)_4]X_2$, $[Pd(en)_2]X_2$, etc. (where M and X have the same meaning as above, and en is ethylenediamine); complex compounds or organic metal compounds, such as $PdCl_2(PhCN)_2$, $PdCl_2(PR_3)_2$, $Pd(CO)Cl$, $Pd(CO)(PR_3)_3$, $Pd(PPh_3)_4$, $PdCl(R)(PPh_3)_2$, $Pd(C_2H_4)(PPh_3)_2$, etc. (where Ph is a phenyl group and R an organic group); complex compounds coordinated with a chelate ligand, such as $Pd(acac)_2$, etc. (acac is an anion of acetylacetone), can be exemplified.

Of these, supported palladium catalysts, such as $Pd/C$, $Pd/Al_2O_3$, etc.; organic acid salts, such as palladium acetate, palladium chloride, etc.; complex compounds, such as $Pd(acac)_2$, $Pd(acac)_3$, $Pd(PPh_3)_4$, etc. are particularly preferable.

Palladium itself can be used as a catalyst, but it is desirable to conduct the reaction with a regeneration of palladium by use of such together with co-catalyst and an oxidizing agent, since using palladium which is expensive in an stoichiometric amount is economically quite disadvantageous. Regeneration means that O-valent palladium is converted to the di-valent oxidation state.

As methods for regeneration, two approaches can be considered, i.e., (1) a method in which palladium catalyst is used with regeneration in the system, and (2) the reaction is conducted using palladium which is pretreated to the di-valent, then the resulting O-valent oxidation state catalyst is separated, and the catalyst is regenerated in an appropriate manner. Of these, approach (1) is preferable, since the reaction can be achieved using a smaller amount of palladium.

Co-catalysts which can be oxidized and regenerated in good efficiency in the presence of oxidizing agent can be used as a co-catalyst in the present invention.

Examples of such co-catalysts include Mn compounds, Co compounds and Cu compounds. Specifically, complex compounds, such as $Mn(acac)_3$, $Mn(acac)_2$, $Co(acac)_2$, $Cu(acac)_2$, Mn-orthohydroxyareneoxime complex, Co-salicylaldehyde ethylenediamine additive complex, phthalocyanine Mu, etc.; organic acid salts, such as Mn acetate, Co acetate, Cu acetate, Mn salicylate, Mn naphthenate, etc.; can be exemplified, as representative but not limitative. Of these, $Mn(acac)_3$, $Mn(acac)_2$, $Mn(OAc)_2$, etc. are particularly preferred. These compounds can be used alone or in combination with each other.

Examples of oxidizing agents used in the present invention include oxygen or air, which are preferable. However, any oxidizing agent can be used. For example, quinone or peroxides can be used. Further, these oxidizing agents can be used by diluting with other inert gas or inert solvents, etc., such as nitrogen, argon, toluene, dichloromethane, 1,4-dioxane, or ethyl acetate.

The amounts of the catalyst used in the present invention is not particularly limited. However, usually from 0.00001 to 10 mole, preferably from 0.0001 to 1 mole in terms of 1 mole of palladium atom is used.

Further, the co-catalyst is used generally in an amount of from 0.01 to 1000 mole, preferably from 0.1 to 100 mole based on the amount of 1 mole of palladium used.

In the present invention, the reaction can be conducted either in the gas phase or the liquid phase. The reaction temperature is usually from 20° to 300° C. The reaction pressure is from 1 to 250 $kg/cm^2$. The reaction time will vary according to the reaction condition, usually from several minutes to several hours.

The present invention is illustrated in greater detail reference to by the following examples, but the present invention is not to be considered as being limited by these examples. Unless otherwise indicated, all parts, percents, ratios and the like are by weight.

EXAMPLE 1

Phenol 5.0 g (53.1 m mole), palladium acetate (II) 7.5 mg (0.0333 m mole), Mn (III) acetylacetonate 11.7 mg (0.0333 m mole) and acetonitrile 20.0 g (487 m mole) were charged to an autoclave of an internal volume of 100 ml. The inside of the system was replaced with carbon monoxide, then carbon monoxide 55 $kg/cm^2$ and oxygen 5 $kg/cm^2$ were charged at room temperature (about 20°–30° C.). The reaction was conducted with stirring at 100° C. for 1 hour, then the contents were analyzed using gas chromatography. As a result, diphenyl carbonate (2.04 m mole) was produced. The yield was 7.7% in terms of phenol.

EXAMPLES 2–4

The same procedures as in Example 1 were used, except that n-butyronitrile 20.0 g, benzonitrile 20.0 g and adiponitrile 20.0 g were used respectively, instead of acetonitrile 20.0 g.

The results obtained are shown in Table 1 below.

COMPARISON EXAMPLE 1

The same procedures as in Example 1 were used, except that phenol 20.0 g (i.e., total phenol was 25 g) was used instead of acetonitrile 20.0 g.

The results obtained are shown in Table 1 below.

TABLE 1

| | Nitrile Compound | Yield of Diphenyl Carbonate* (yield per batch) |
|---|---|---|
| Comp. Example 1 | — | 0.3% |
| Example 1 | acetonitrile | 7.7% |
| Example 2 | n-butyronitrile | 4.4% |
| Example 3 | benzonitrile | 4.6% |
| Example 4 | adiponitrile | 1.1% |

*Yield is based on phenol as raw material

EXAMPLES 5-10

Amounts of Nitrile Compounds and Yield

Phenol A g, acetonitrile B g (provided that A+B=25 g) were charged to an autoclave of an internal volume of 100 ml, then palladium acetate (1/3000 mole), based on the amount of 1 mole of phenol, Mn acetylacetonate (5 mole amounts based on the amount of 1 mole of palladium acetate) were charged. Then the inside of the system was replaced with carbon monoxide, then carbon monoxide 55 kg/cm$^2$ and oxygen 5 kg/cm$^2$ were charged at room temperature. The reaction was conducted with stirring at 100° C. for 1 hour, and the contents were analyzed using gas chromatography. The results obtained are shown in Table 2 below.

COMPARISON EXAMPLE 2

In Examples 5-10, the reaction was conducted with B=0 g (i.e., acetonitrile was 0). The results obtained are shown in Table 2 below.

TABLE 2

| | A:B (weight ratio) | Yield of Diphenyl* Carbonate (yield per batch) |
|---|---|---|
| Comp. Example 2 | 1:0 | 1.0% |
| Example 5 | 100:1 | 1.4% |
| Example 6 | 10:1 | 4.5% |
| Example 7 | 4:1 | 6.9% |
| Example 8 | 1:1 | 11.3% |
| Example 9 | 1:4 | 11.5% |
| Example 10 | 1:10 | 8.5% |

*Yield is based on phenol of raw material

EXAMPLES 11-15

Effect of Catalyst

Phenol 5.0 g (53.1 m mole), catalyst as shown in Table 3 below (0.0333 m mole), Mn (III) acetylacetonate 58.7 mg (0.1667 m mole) and acetonitrile 20.0 g (487 m mole) were charged to an autoclave of an internal volume of 100 ml. The inside of the system was replaced with carbon monoxide, then carbon monoxide 55 kg/cm$^2$ and oxygen 5 kg/cm$^2$ were charged at room temperature. The reaction was conducted with stirring at 100° C. for 1 hour, then the contents were analyzed by gas chromatography. The results obtained are shown in Table 3 below.

TABLE 3

| | Catalyst | Yield of Diphenyl* Carbonate (yield per batch) |
|---|---|---|
| Example 11 | Pd(OAc)$_2$ | 13.8% |
| Example 12 | PdCl$_2$ | 7.2% |
| Example 13 | Pd(acac)$_2$ | 13.1% |
| Example 14 | Pd(PPh$_3$)$_4$ | 5.2% |
| Example 15 | Pd/C (5%) | 12.6% |

*Yield is based on phenol as a raw material;
OAc is acetate anion.
acac is acetylacetone anion.
Ph is a phenyl group

EXAMPLES 16-18

Effect of Co-Catalyst

Phenol 5.0 g (53.1 m mole), palladium (II) acetate 7.5 mg (0.0333 m mole), co-catalyst as shown in Table 4 (0.1667 m mole) and acetonitrile 20.0 g (487 m mole) were charged in an autoclave of an internal volume of 100 ml. The inside of the system was replaced with carbon monoxide, then carbon monoxide 55 kg/cm$^2$ and oxygen 5 kg/cm$^2$ were charged under room temperature. The reaction was conducted with stirring at 100° C. for 1 hour, then the contents were analyzed using gas chromatography. The results obtained are shown in Table 4 below.

TABLE 4

| | Catalyst | Yield of Diphenyl* Carbonate (yield per batch) |
|---|---|---|
| Example 16 | Mn(acac)$_3$ | 13.8% |
| Example 17 | Mn(acac)$_2$ | 12.6% |
| Example 18 | Mn(OAc)$_2$ · 4 hydrate | 6.3% |

*Yield based on phenol of raw material.
OAc, acac and Ph have the same meaning as in Table 3.

According to the present invention, an aromatic carbonate can be prepared in an extremely simple system, which is not industrially difficult and which does not employ expensive compounds, such as amines, quinone or quaternary salts. Further, the present invention has excellent industrial effects, i.e., the cost required for separation and purification is reduced, since the preparation and purification procedures are not complex.

While the invention has been described in detail and with reference to specific embodiments, it will be apparent to one skilled in the art that changes and modifications can be made therein without departing from the spirit and scope thereof.

What is claimed is:

1. A process for producing an aromatic carbonate which comprises:
  reacting
    (a) an aromatic hydroxy compound with
    (b) carbon monoxide in the presence of
    (c) an oxidation agent,
    (d) a catalyst comprising (i) palladium, per se, (ii) a palladium compound or (iii) a support impregnated with palladium or a palladium compound,
    (e) a co-catalyst comprising a manganese compound, a cobalt compound or a copper compound, and
    (f) at least one nitrile compound as a solvent in an amount of 0.1 to 10 moles per mole of aromatic hydroxy compound (a),
  at a temperature of 20° to 300° C.

2. The process for producing an aromatic carbonate as claimed in claim 1, wherein the aromatic hydroxy compound (a) is phenol.

3. The process for producing an aromatic carbonate as claimed in claim 1, wherein the oxidation agent (c) is oxygen or air.

4. The process for producing an aromatic carbonate as claimed in claim 1, wherein the nitrile compound (f) is at least one compound selected from the group consisting of an aliphatic nitrile, an aromatic nitrile and an aromatic-aliphatic nitrile.

5. A process for producing an aromatic carbonate which comprises:

reacting
- (a) an aromatic hydroxy compound with
- (b) carbon monoxide in the presence of
- (c) an oxidation agent,
- (d) a catalyst comprising (i) palladium, per se, (ii) a palladium compound or (iii) a support impregnated with palladium or a palladium compound,
- (e) a co-catalyst comprising a manganese compound, a cobalt compound or a copper compound, and
- (f) at least one compound selected from the group consisting of acetonitrile, n-butyronitrile and benzonitrile as a solvent in an amount of 0.1 to 10 moles per mole of aromatic hydroxy compound (a), at a temperature of 20° to 300° C.

6. The process for producing an aromatic carbonate as claimed in claim 1, wherein the amount of nitrile compound (f) is 0.001 to 100 moles per mole of aromatic hydroxy compound (a).

7. The process for producing an aromatic carbonate as claimed in claim 1, wherein the amount of nitrile compound (f) is 0.1 to 10 moles per mole of aromatic hydroxy compound (a).

8. The process for producing an aromatic carbonate as claimed in claim 1, wherein the amount of co-catalyst (e) is 0.1 to 100 moles per mole of palladium atom in the palladium catalyst (d).

9. The process for producing an aromatic carbonate as claimed in claim 1, wherein the palladium catalyst (d) is at least one member selected from the group consisting of Pd/C, Pd/Al$_2$O$_3$, Pd(OAc)$_2$, PdCl$_2$, Pd(acac)$_2$ and Pd(PPh$_3$)$_4$.

10. The process for producing an aromatic carbonate as claimed in claim 1, wherein the co-catalyst (e) is a manganese compound.

11. The process for producing an aromatic carbonate as claimed in claim 1, wherein the co-catalyst (e) is at least one compound selected from the group consisting of Mn(acac)$_2$, Mn(acac)$_3$ and Mn(OAc)$_2$.

12. A process for producing an aromatic carbonate which comprises:

reacting
- (a) an aromatic hydroxy compound with
- (b) carbon monoxide in the presence of
- (c) an oxidation agent,
- (d) a catalyst comprising: (i) palladium, per se, (ii) a palladium compound or (iii) a support impregnated with palladium or a palladium compound, wherein the amount of palladium catalyst is 0.0001 to 10 moles of palladium atom per mole of aromatic hydroxy compound (a),
- (e) a co-catalyst comprising a manganese compound, a cobalt compound or copper compound, and
- (f) at least one nitrile compound as a solvent in an amount of 0.1 to 10 moles per mole of aromatic hydroxy compound (a), at a temperature of 20° to 300° C.

* * * * *